United States Patent
Nimura et al.

(10) Patent No.: US 11,590,334 B2
(45) Date of Patent: Feb. 28, 2023

(54) BLOOD CIRCUIT ADAPTER SET AND BLOOD CIRCUIT

(71) Applicant: NIKKISO CO., LTD., Tokyo (JP)

(72) Inventors: Hiroshi Nimura, Makinohara (JP);
Yoshimichi Masuda, Makinohara (JP);
Masato Fujiwara, Makinohara (JP)

(73) Assignee: NIKKISO CO., LTD., Tokyo (JP)

( * ) Notice: Subject to any disclaimer, the term of this patent is extended or adjusted under 35 U.S.C. 154(b) by 992 days.

(21) Appl. No.: 16/324,740

(22) PCT Filed: Aug. 7, 2017

(86) PCT No.: PCT/JP2017/028625
§ 371 (c)(1),
(2) Date: Feb. 11, 2019

(87) PCT Pub. No.: WO2018/030354
PCT Pub. Date: Feb. 15, 2018

(65) Prior Publication Data
US 2019/0184150 A1 Jun. 20, 2019

(30) Foreign Application Priority Data
Aug. 9, 2016 (JP) .............................. JP2016-156943

(51) Int. Cl.
*A61M 39/10* (2006.01)
*A61M 1/36* (2006.01)

(52) U.S. Cl.
CPC .......... *A61M 39/10* (2013.01); *A61M 1/3638* (2014.02); *A61M 1/3644* (2014.02);
(Continued)

(58) Field of Classification Search
CPC . A61M 39/10; A61M 2039/1077; F16L 35/00
See application file for complete search history.

(56) References Cited

U.S. PATENT DOCUMENTS

| 4,619,640 A | * | 10/1986 | Potolsky | ............... | A61M 39/10 128/912 |
| 4,967,173 A | | 10/1990 | Watson | | |

(Continued)

FOREIGN PATENT DOCUMENTS

| CN | 101641122 A | 2/2010 |
| CN | 103282062 A | 9/2013 |

(Continued)

OTHER PUBLICATIONS

Nov. 7, 2017 International Search Report issued in International Patent Application No. PCT/JP2017/028625.

(Continued)

*Primary Examiner* — David Bochna
(74) *Attorney, Agent, or Firm* — Oliff PLC (57) ABSTRACT

An adapter set that is attached to artery-side and vein-side shunt connectors-that are provided on a blood circuit. The adapter set includes: an artery-side adapter that has one end thereof connected to the artery-side shunt connector, has the other end thereof connected to a drainage port that is provided on the outside of the blood circuit, and thereby connects the artery-side shunt connector and the drainage port fluid tight; and a vein-side adapter that has one end thereof connected to the vein-side shunt connector, has the other end thereof connected to a supply port that is provided on the outside of the blood circuit, and thereby connects the vein-side shunt connector and the supply port fluid tight. The structure of the other end of the artery-side adapter and the structure of the other end of the vein-side adapter are different.

3 Claims, 6 Drawing Sheets

(52) U.S. Cl.
CPC ........ *A61M 1/3647* (2014.02); *A61M 1/3649* (2014.02); *A61M 2039/1077* (2013.01); *A61M 2039/1094* (2013.01); *A61M 2205/0288* (2013.01); *A61M 2205/276* (2013.01)

(56) References Cited

U.S. PATENT DOCUMENTS

| | | | |
|---|---|---|---|
| 5,725,511 A | 3/1998 | Urrutia | |
| 5,762,805 A | 6/1998 | Truitt et al. | |
| 5,776,345 A | 7/1998 | Truitt et al. | |
| 5,947,937 A * | 9/1999 | Urrutia | A61M 39/10 604/533 |
| 6,402,207 B1 * | 6/2002 | Segal | A61M 39/10 285/330 |
| 2003/0010717 A1 | 1/2003 | Brugger et al. | |
| 2004/0217586 A1 * | 11/2004 | Mastropaolo | F16L 35/00 285/124.1 |
| 2005/0230314 A1 | 10/2005 | Kim et al. | |
| 2005/0267445 A1 * | 12/2005 | Mendels | A61M 39/10 604/534 |
| 2006/0100564 A1 | 5/2006 | Sano et al. | |
| 2007/0076401 A1 * | 4/2007 | Carrez | A61M 39/10 361/816 |
| 2008/0228125 A1 * | 9/2008 | Brugger | A61M 39/10 604/6.16 |
| 2008/0318456 A1 * | 12/2008 | Yow | A61M 39/10 439/157 |
| 2009/0076433 A1 | 3/2009 | Folden et al. | |
| 2009/0099552 A1 * | 4/2009 | Levy | A61M 39/10 604/533 |
| 2010/0078385 A1 | 4/2010 | Kawarabata et al. | |
| 2013/0303963 A1 | 11/2013 | Breuch et al. | |
| 2014/0048460 A1 | 2/2014 | Paolini et al. | |
| 2015/0151036 A1 | 6/2015 | Furuhashi et al. | |
| 2016/0250405 A1 | 9/2016 | Kogoshi et al. | |
| 2017/0072122 A1 | 3/2017 | Mochizuki | |
| 2017/0232180 A1 | 8/2017 | Umeda et al. | |
| 2018/0021512 A1 * | 1/2018 | Fukuoka | A61M 39/10 604/404 |
| 2018/0110914 A1 | 4/2018 | Fujiwara et al. | |
| 2019/0117950 A1 * | 4/2019 | Carlsson | A61M 39/10 |
| 2019/0184150 A1 | 6/2019 | Nimura et al. | |
| 2020/0276381 A1 * | 9/2020 | Gutzler | A61M 39/10 |
| 2021/0162124 A1 * | 6/2021 | Nakagawa | A61M 39/10 |
| 2021/0187265 A1 * | 6/2021 | Schuler | A61M 39/10 |

FOREIGN PATENT DOCUMENTS

| | | |
|---|---|---|
| EP | 2 142 234 B1 | 1/2013 |
| EP | 2197513 B1 | 4/2017 |
| EP | 3266496 A2 | 1/2018 |
| JP | H03-105264 A | 5/1991 |
| JP | H06-315530 A | 11/1994 |
| JP | H07-313590 A | 12/1995 |
| JP | 2003-180823 A | 7/2003 |
| JP | 2003-531687 A | 10/2003 |
| JP | 2006-130063 A | 5/2006 |
| JP | 2006-175103 A | 7/2006 |
| JP | 2007-512885 A | 5/2007 |
| JP | 2007-215557 A | 8/2007 |
| JP | 2010-538800 A | 12/2010 |
| JP | 2012-034992 A | 2/2012 |
| JP | 5399218 B2 | 1/2014 |
| JP | 2015-213642 A | 12/2015 |
| JP | 2016-000367 A | 1/2016 |
| JP | 2020048948 A * | 4/2020 ............ A61M 39/10 |
| WO | 2005/118485 A1 | 12/2005 |
| WO | 2010/042666 A2 | 4/2010 |
| WO | 2012/085644 A1 | 6/2012 |
| WO | 2015/068833 A1 | 5/2015 |
| WO | 2016/067946 A1 | 5/2016 |
| WO | 2018/030354 A1 | 2/2018 |

OTHER PUBLICATIONS

Aug. 20, 2021 Final Office Action Issued in U.S. Appl. No. 16/321,767.
Feb. 9, 2021 Office Action issued in U.S. Appl. No. 16/321,767.
Oct. 24, 2017 Search Report issued in International Patent Application No. PCT/JP2017/028623.
Jan. 29, 2019, U.S. Appl. No. 16/321,767 in the name of Hiroshi Nimura et al.
Jun. 27, 2019 European Search Report issued in European Patent Application No. 17839425.0.
Jan. 30, 2020 Extended European Search Report Issued in European Patent Application No. 17839424.3.
Nov. 21, 2019 Extended European Search Report issued in European Patent Application No. 19189412.0.
Sep. 3, 2020 Office Action issued in Chinese Patent Application No. 201780047017.4.
May 7, 2021 Office Action issued in Chinese Patent Application No. 201780047017.4.
May 25, 2021 Office Action issued in Japanese Patent Application No. 2018-533462.
Jan. 26, 2022 Notice of Allowance issued in U.S. Appl. No. 16/321,767.
Dec. 14, 2021 Office Action issued in Japanese Patent Application No. 2018-533462.

* cited by examiner

BLOOD CIRCUIT ADAPTER SET AND BLOOD CIRCUIT

TECHNICAL FIELD

The present invention relates to a blood circuit adapter set provided with two adapters to be connected to connectors provided on a blood circuit, and a blood circuit having the adapters.

BACKGROUND ART

In the related art, blood purification that purifies blood from a patient outside the body and returns the blood into the body is widely known. In such blood purification, a blood circuit and a blood purifier are used. The blood circuit and the blood purifier are discarded and replaced every time of usage. The blood circuit includes two connectors configured to allow connection of puncture needles. Through the puncture needles connected to these two connectors, blood is collected from a patient, and the blood after purification is flowed back to the patient.

In the normal blood purification, priming is performed prior to a treatment. In the priming, interiors of the blood circuit and the blood purifier are filled with a liquid. When performing the priming, the connectors of the blood circuit need to be connected to ports of a supply part and a discharge part for the priming liquid. However, the two connectors are similar in appearance in many cases, and thus have a risk of being connected to wrong ports, that is, there is a probability of erroneous connection.

CITATION LIST

Patent Literature

Patent Literature 1: JP 2016-000367 A
Patent Literature 2: JP 2015-213642 A

SUMMARY

Technical Problem

In order to prevent such an erroneous connection, forming the connectors into specific shapes to limit connection to only a corresponding port is conceivable. However, after the priming, the puncture needles need to be connected to the connectors, and many of the puncture needles have a standard-based shape. When the connectors of the specific shape are employed for preventing the erroneous connection, versatile standard-based puncture needles cannot be connected, and thus general versatility of the blood circuit is impaired.

Patent Literatures 1 and 2 disclose a technique for preventing the erroneous connection of connectors by integrating a plurality of transfusion lines with a resin member and making arrangement of the plurality of transfusion lines and a shape of the resin member asymmetrical, in order to prevent the erroneous connection of the transfusion lines. In this case, a versatile shape may be employed for the connector itself provided on the respective transfusion lines, and thus a high versatility of the connectors is achieved. However, with the technology disclosed in Patent Literatures 1 and 2, provision of the resin member that surrounds the periphery of the connector is inevitable. The resin member becomes an obstacle during handling of the blood circuit during the treatment, and thus operability may be lowered.

Accordingly, it is an advantage of the present invention to provide an adapter set and a blood circuit capable of preventing an erroneous connection with higher reliability while maintaining general versatility and operability.

Solution to Problem

An adapter set of the present invention is a blood circuit adapter set to be attached to first and second connectors provided on a blood circuit, including: a first adapter having a first end and a second end, wherein when the first adapter is connected at the first end thereof to the first connector and connected at the second end thereof to a first port provided outside the blood circuit, and the first adapter allows communication between the first connector and the first port in a liquid-tight manner; and a second adapter having a first end and a second end, wherein when the second adapter is connected at the first end thereof to the second connector and connected at the second end thereof to a second port provided outside the blood circuit, and the second adapter allows communication between the second connector and the second port in a liquid-tight manner, wherein the second end of the first adapter and the second end of the second adapter have different structures to disable at least one of connection between the second end of the first adapter and the second port and connection between the second end of the second adapter and the first port.

In a preferred mode, the first connector and the second connector allow connection of the puncture needles of the same type, and the first end of the first adapter and the first end of the second adapter have the same structure.

In another preferred mode, the second end of the first adapter and the second end of the second adapter have different shapes from each other.

In still another preferred mode, the first connector and the second connector may be connected to the first and second ports in a state of being integrally coupled to each other.

A blood circuit according to another aspect of the present invention includes: a blood line in which blood flows; a first connector and a second connector attached to the blood line; a first adapter having a first end and a second end, wherein when the first adapter is connected at the first end thereof to the first connector and connected at the second end thereof to a first port provided outside the blood circuit, and the first adapter allows communication between the first connector and the first port in a liquid-tight manner; and a second adapter having a first end and a second end, wherein when the second adapter is connected at the first end thereof to the second connector and connected at the second end thereof to a second port provided outside the blood circuit, and the second adapter allows communication between the second connector and the second port in a liquid-tight manner, wherein the second end of the first adapter and the second end of the second adapter have different structures to disable at least one of connection between the second end of the first adapter and the second port and connection between the second end of the second adapter and the first port.

Advantageous Effects of Invention

According to the present invention, the structures of the second ends of the first and second adapters (ends connected to the first and second ports) connected to the first and second connectors are different from each other, and erroneous connection is effectively prevented. In contrast, since the first and second connectors do not have to have a specific shape, versatility and operability of the blood circuit may be maintained.

DESCRIPTION OF EMBODIMENT

Figure 1:
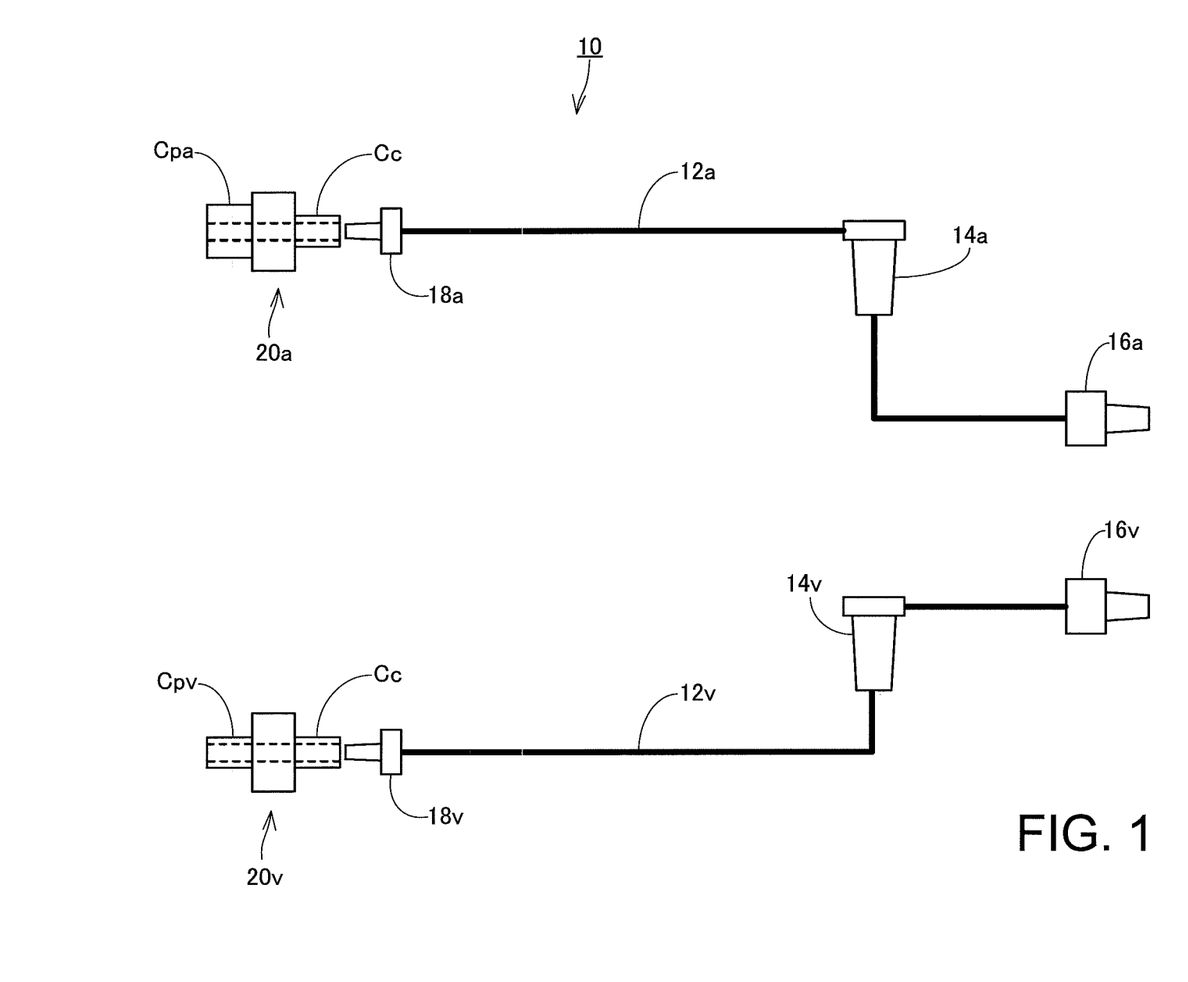
FIG. 1 is a drawing illustrating a configuration of a blood circuit according to an exemplary embodiment of the present invention.
Figure 2:
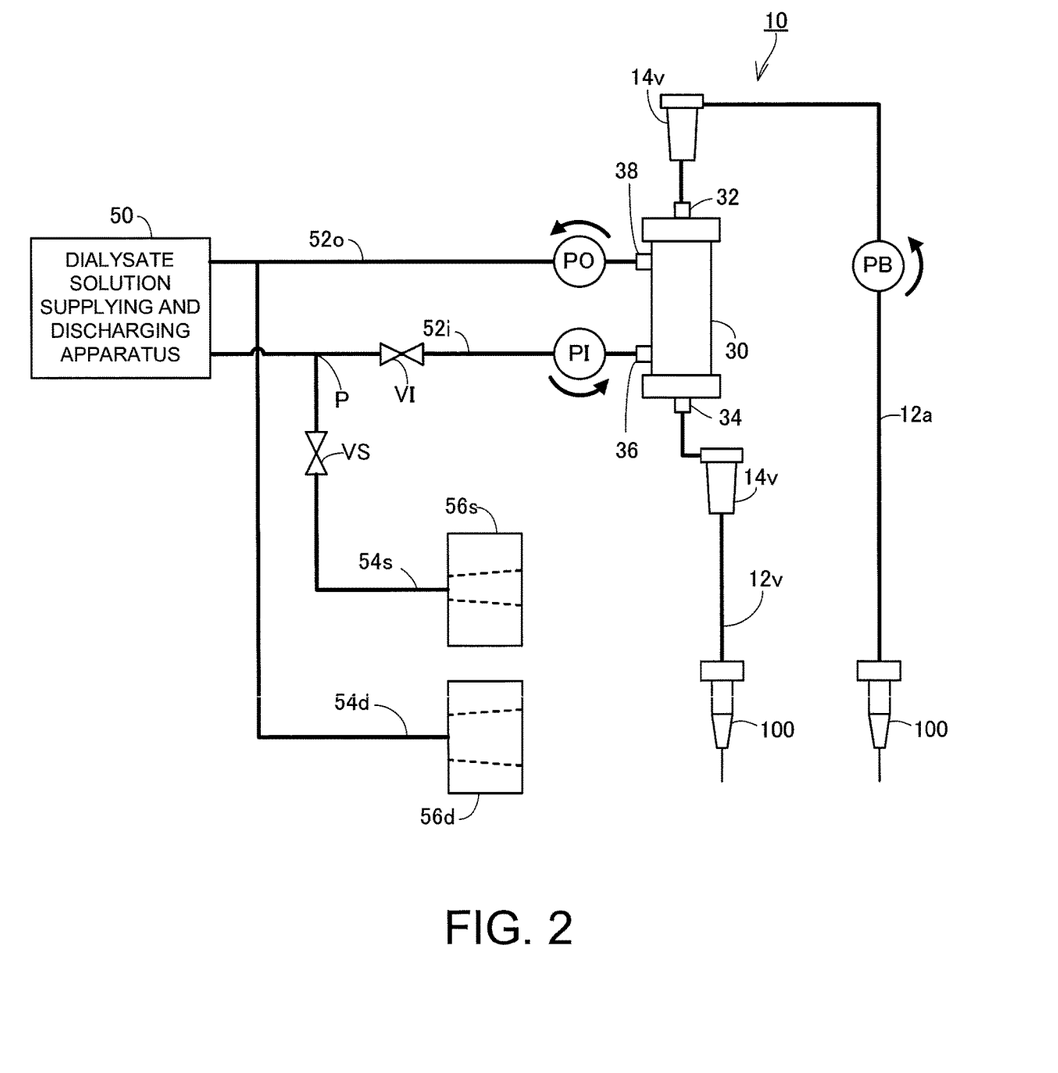
FIG. 2 is a drawing illustrating a state of performing a dialysis treatment by using the blood circuit.
Figure 3:
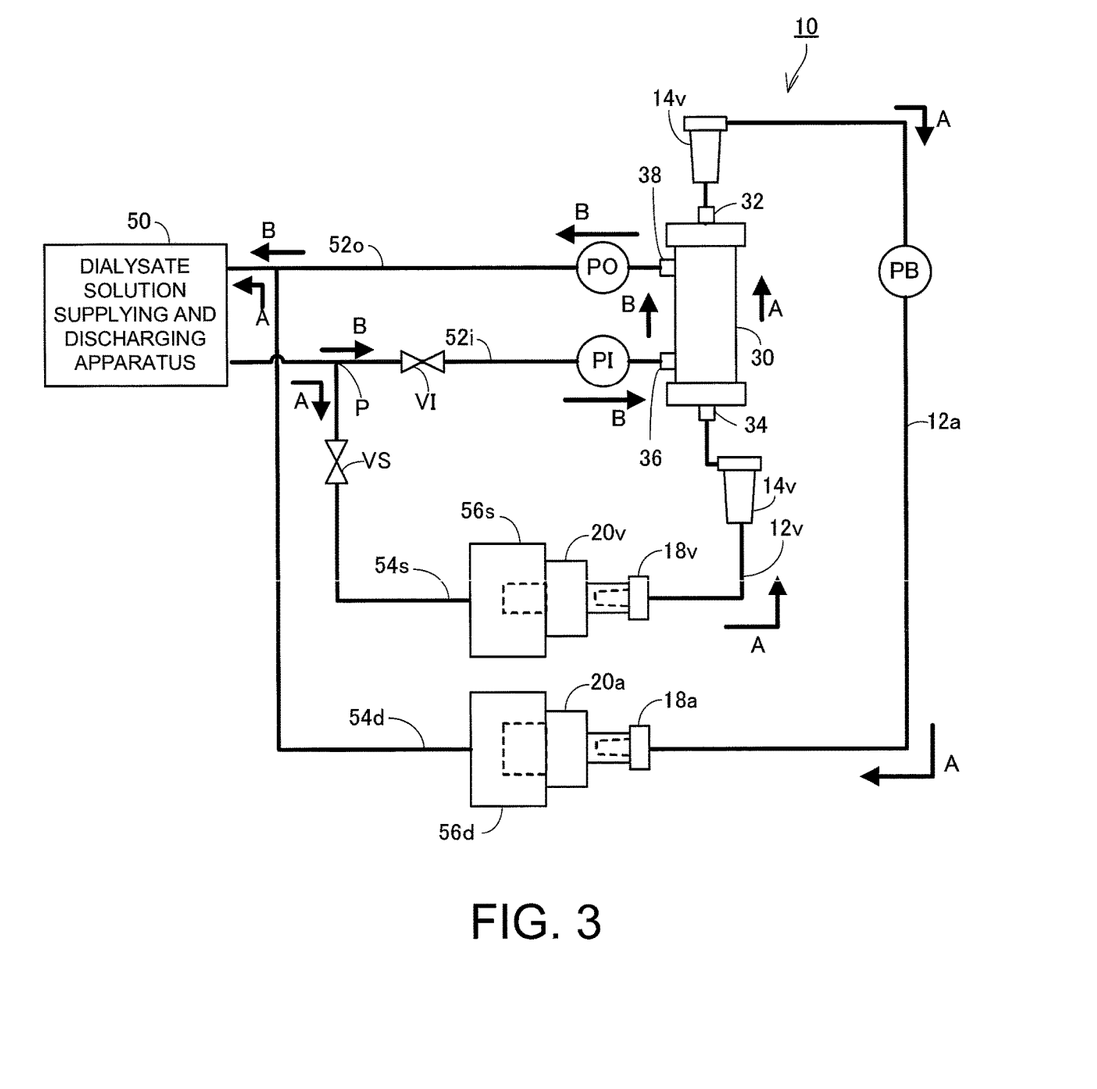
FIG. 3 is a drawing illustrating a state of performing a priming process by using the blood circuit.
Figure 4:
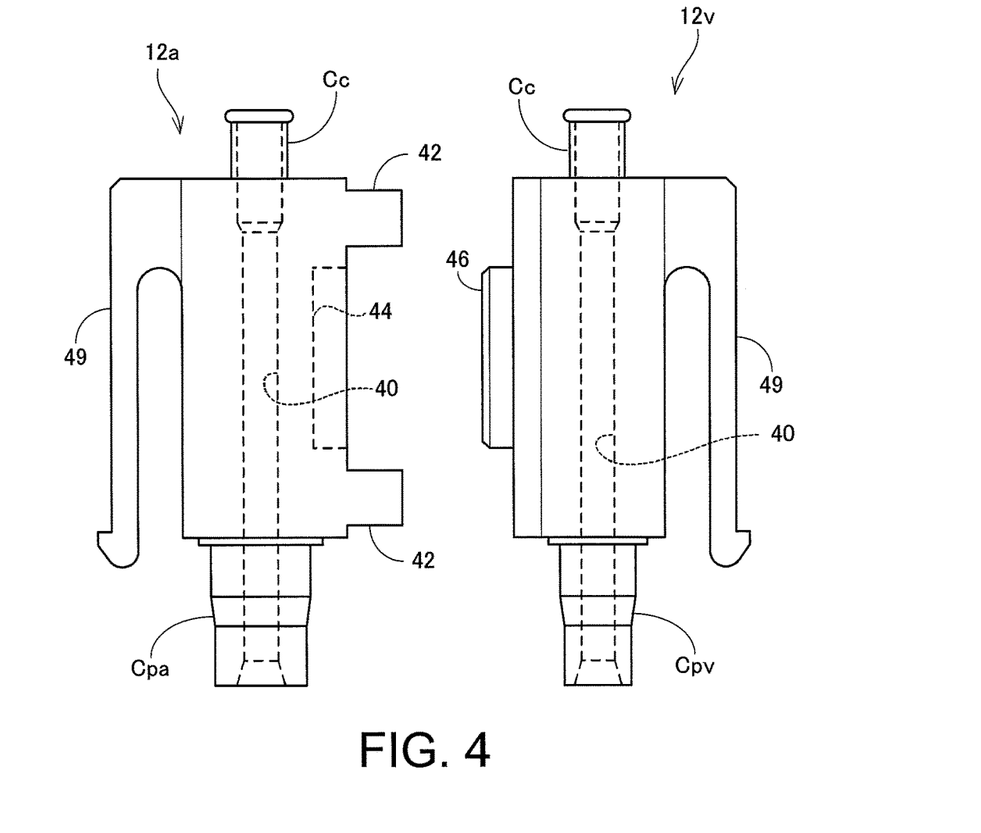
FIG. 4 is a front view of an adapter set.
Figure 5:
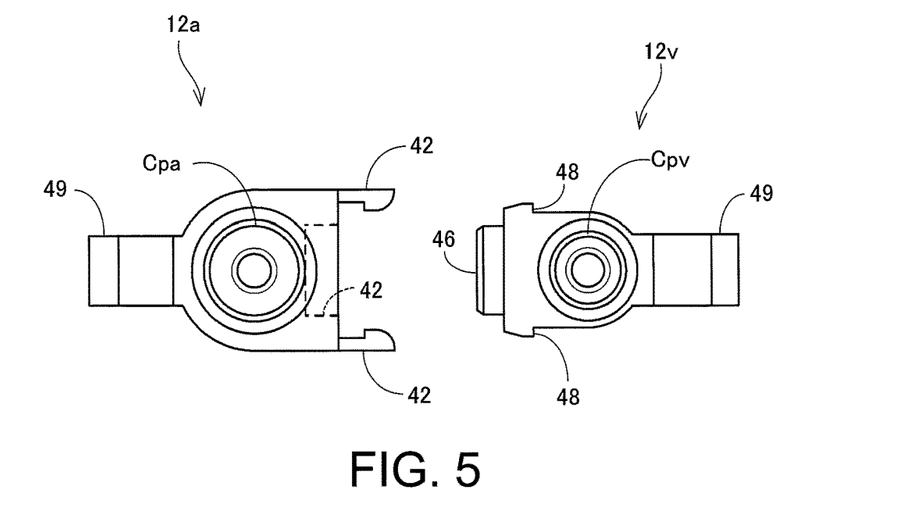
FIG. 5 is a drawing illustrating the adapter set viewed from a port connecting portion side.

Referring now to the drawings, an exemplary embodiment of the present invention will be described. FIG. 1 is a schematic configuration drawing illustrating a blood circuit 10 according to an exemplary embodiment of the present invention. FIG. 2 is a drawing illustrating a state of performing a dialysis treatment using the blood circuit 10, and FIG. 3 is a drawing illustrating a state of performing a priming process using the blood circuit 10. FIG. 4 and FIG. 5 are drawings illustrating an example of adapters 20a, 20v to be connected to shunt connectors 18.

The blood circuit 10 is a flow channel in which a liquid such as blood or a priming liquid flows, and is used for performing blood purification such as hemodialysis. The blood circuit 10 is a disposable member which is discarded and replaced every time after usage, together with the blood purifier such as a dialyzer, described later. The blood circuit 10 is shipped after having been sterilized, in a state of being sealed in a sterile bag (not illustrated). For use, an operator opens the sterile bag and takes out the blood circuit 10, and assembles the blood circuit 10 with a dialysis apparatus together with the dialyzer.

The blood circuit 10 of the present exemplary embodiment includes an artery-side blood line 12a and a vein-side blood line 12v. In the following description, when the blood lines do not have to be discriminated between the artery side and the vein side, they are simply referred to as "blood lines 12" with subscript letters a and v omitted. The same applies to other members. In this specification, a side of a puncture needle for blood removal (blood drawing) is referred to as "artery side" and a side of the puncture needle for returning blood is referred to as "vein side". Therefore, as used herein the terms "artery side" and "vein side" are not defined by whether the blood vessel to be punctured is an artery or a vein. During the treatment, the artery-side blood line 12a is a line used for blood removal, and thus blood collected from the patient flows therein. The vein-side blood line 12v is a line used for returning the blood, and thus blood having passed through the blood purifier flows therein. Both of the artery-side blood line 12a and the vein-side blood line 12v are made of a flexible tube. An artery-side shunt connector 18a (first connector) which allows connection of a puncture needle 100 is connected to one end of the artery-side blood line 12a, and an artery-side dialyzer connector 16a which allows connection to a blood entry port 32 of a dialyzer 30 is secured to the other end of the artery-side blood line 12a. The artery-side blood line 12a is provided in the middle thereof with an air-trap chamber 14a configured to temporarily store blood to expel air bubbles.

The vein-side blood line 12v has a similar configuration. A vein-side shunt connector 18v (second connector) which allows connection of a puncture needles 100 is connected to one end of the vein-side blood line 12v, and a vein-side dialyzer connector 16v which allows connection to a blood exit port 34 of a dialyzer 30 is secured to the other end of the vein-side blood line 12v. The vein-side blood line 12v is also provided in the middle thereof with an air-trap chamber 14v configured to temporarily store blood to expel air bubbles. The dialyzer connector 16 and the air trap chamber 14 will not be described in detail in this specification because a known technique may be used. In the present exemplary embodiment, the air trap chamber 14 is provided both on the vein side and on the artery side. However, at least one of these may be omitted. The artery-side shunt connector 18a and the vein-side shunt connector 18v both have a structure which allows connection of the standard-based versatile puncture needles 100, and both have the same shape.

The blood circuit 10 is further provided with an adapter set including an artery-side adapter 20a (first adapter) and a vein-side adapter 20v (second adapter). The artery-side adapter 20a is connected to the artery-side shunt connector 18a, and the vein-side adapter 20v is connected to the vein-side shunt connector 18v both in a disconnectable manner. In FIG. 1, the shunt connectors 18 and the adapters 20 are illustrated separately for the sake of easy visual understanding. In fact, however, the blood circuit 10 is shipped in a state in which the corresponding adapters 20 are attached respectively to the shunt connectors 18. In other words, a suitable one of the adapters 20 is attached to each of the shunt connectors 18 already when the operator starts to use the blood circuit 10. Therefore, the operator does not have to think which one of the adapters 20 is to be attached to which one of the shunt connectors 18, and thus erroneous connection between the shunt connector 18 and the adapter 20 is considered to be almost eliminated.

The artery-side adapter 20a and the vein-side adapter 20v both have a substantially tubular shape having a flow channel penetrating therethrough in an axial direction. The first end of the artery-side adapter 20a is connected to the artery-side shunt connector 18a, and the second end thereof is configured to be connectable to a discharge port 56d (first port), described later (See FIG. 2 and FIG. 3). When the discharge port 56d is connected to the second end of the artery-side adapter 20a attached to the artery-side shunt connector 18a, the artery-side shunt connector 18a and the discharge port 56d, and thus the artery-side blood line 12a and a discharge line 54d, communicate with each other in a liquid-tight manner. In the same manner, the first end of the vein-side adapter 20v is connected to the vein-side shunt connector 18v, and the second end thereof is connectable to a supply port 56s (second port) described later. When the supply port 56s is connected to the second end of the vein-side adapter 20v attached to the vein-side shunt connector 18v, the vein-side shunt connector 18v and the supply port 56s, and thus the vein-side blood line 12v and a supply line 54s, communicate with each other in a liquid-tight manner Each of the adapters 20 includes one of connector connecting portions Cc to be connected to the corresponding one of the shunt connectors 18 and one of port connecting portions Cp to be connected to corresponding one of the supply and discharge ports 56. In the present exemplary embodiment, the respective connector connecting portions Cc of the artery-side adapter 20a and the vein-side adapter 20v have the same configuration, and respective port connecting portions Cpa and Cpv have different configurations. Specifically, the port connecting portion Cpa of the artery-side adapter 20a has a diameter larger than the port connecting portion Cpv of the vein-side adapter 20v. Such a configuration is employed for preventing erroneous connection that may occur when the blood circuit 10 and the line provided on the dialysis apparatus are connected. This will be described in detail below.

Referring to FIG. 2, a state of performing the dialysis treatment by using the blood circuit 10 will be described first. For performing the dialysis treatment, the blood circuit 10 and the dialyzer 30 are attached to the dialysis apparatus in advance. The dialysis apparatus circulates blood outside the body and supplies and discharges dialysate solution under the instruction of the operator. The dialysis apparatus is provided with a blood pump PB provided in the middle of the artery-side blood line 12a and is configured to feed blood toward the dialyzer 30. With the blood pump PB driven normally, blood is fed downstream (toward the dialyzer 30). As described later in detail, the blood pump PB may be driven reversely to cause the priming liquid (for example, dialysate solution) to flow at the time of the priming process. The configuration of the blood pump PB is not specifically limited, but in the present exemplary embodiment, the blood pump PB is a squeezing-type tube pump. The blood pump PB feeds blood, priming liquid and the like by squeezing the artery-side blood line 12a made of a flexible tube. Note that an arrow indicated in the vicinity of the blood pump PB in FIG. 2 indicates a direction of the normal driving of the blood pump PB.

The dialysis apparatus may further be provided with a dialysate solution supplying and discharging apparatus 50 configured to supply and discharge the dialysate solution. An introduction line 52i and an outlet line 52o are connected to the dialysate solution supplying and discharging apparatus 50. The introduction line 52i is a line configured to supply the dialysate solution from the dialysate solution supplying and discharging apparatus 50 to the dialyzer 30, and is provided with an introduction pump PI in the middle thereof. The outlet line 52o is a line configured to discharge the dialysate solution from the dialyzer 30 to the dialysate solution supplying and discharging apparatus 50, and is provided with an outlet pump PO in the middle thereof. The introduction pump PI and the outlet pump PO may have any configuration as long as they are capable of feeding the dialysate solution. Therefore, the introduction pump PI and the outlet pump PO may be configured to be driven independently, such as tube pumps, or may be configured to be composite pump driven in conjunction with each other. In FIG. 2, arrows indicated in the vicinities of the introduction pump PI and the outlet pump PO indicate the direction of normal driving of these pumps.

The introduction line 52i is bifurcated at a branch point P in the middle thereof and constitutes the supply line 54s. The discharge line 54d joins the middle of the outlet line 52o. In the following description, when these lines do not have to be discriminated between supply and discharge, they are simply referred to as "supplying and discharging lines 54" with the subscript letters s and e omitted. The same applies to other members. The supply line 54s and the discharge line 54d are both used in the priming process described later. The supply port 56s and the discharge port 56d are provided at ends thereof with the supply line 54s and the discharge line 54d. The supply port 56s receives a supply of the priming liquid and allows connection of the vein-side adapter 20v described above. The discharge port 56d receives an input of priming liquid after use and allows connection of the artery-side adapter 20a described above (see FIG. 3). However, as illustrated in FIG. 2, nothing is connected to the supply and discharge ports 56s and 56d during the dialysis treatment. As described above, the port connecting portions Cpa and Cpv of the vein-side adapter 20v and the artery-side adapter 20a have different shapes from each other and thus the supply and discharge ports 56 corresponding to these adapters 20 have different shapes from each other. Specifically, an insertion port of the discharge port 56d that allows connection of the artery-side adapter 20a has a diameter larger than the supply port 56s which allows connection of the vein-side adapter 20v.

The dialysis apparatus further includes an introduction valve VI and a supply valve VS for switching the destination of supply of the dialysate solution supplied from the dialysate solution supplying and discharging apparatus 50. The introduction valve VI is provided on the introduction line 52i on the downstream side (dialyzer 30 side) of the branch point P, and the supply valve VS is provided in the middle of the supply line 54s. The dialysate solution supplied from the dialysate solution supplying and discharging apparatus 50 is supplied to the dialyzer 30 by opening the introduction valve VI and closing the supply valve VS, and is supplied to the supply port 56s by closing the introduction valve VI and opening the supply valve VS. Note that the introduction valve VI and the supply valve VS may be omitted or modified when the destination of supply of the dialysate solution can be switched. For example, a three-direction valve may be provided at the branch point P instead of the introduction valve VI and the supply valve VS. When the squeezing-type tube pump is not driven, the tube may be closed. Therefore, the squeezing-type tube pump may be employed as the introduction pump PI and the introduction pump PI may be made to function as the introduction valve VI.

The blood circuit 10 and the dialyzer 30 are set in the dialysis apparatus described thus far. The blood circuit 10 is a flow channel including the artery-side blood line 12a and the vein-side blood line 12v as described above, and is provided with the air trap chamber 14 for discharging air bubbles in the middle thereof. The blood circuit 10 is set in the dialysis apparatus so that the blood pump PB is positioned in the middle of the artery-side blood line 12a.

The dialyzer 30 is a blood purifier configured for purifying blood. The dialyzer 30 has a substantially cylindrical container and includes a hollow fiber membrane in the interior of the container. The blood entry port 32 and the blood exit port 34 are provided at both ends of the dialyzer 30 in the axial direction. The artery-side blood line 12a is connected to the blood entry port 32 and the vein-side blood line 12v is connected to the blood exit port 34, respectively. The dialyzer 30 is provided on a peripheral surface thereof with an introduction port 36 and an outlet port 38. The introduction line 52i is connected to the introduction port 36, and the outlet line 52o is connected to an outlet port 38, respectively.

As illustrated in FIG. 2, the adapters 20 attached to the shunt connectors 18 are removed and the puncture needles 100 are attached to the shunt connectors 18 instead for the dialysis treatment. The puncture needles 100 on the artery side and the vein side are both versatile tools in conformance with the specific standard, and have connecting portions of the same shape.

For the dialysis treatment, the blood pump PB is normally driven with the puncture needles 100 punctured into blood vessels of the patient. The introduction valve VI is opened and the supply valve VS is closed, and the introduction pump PI and the outlet pump PO are normally driven to supply and discharge the dialysate solution to and from the dialyzer 30. Blood of the patient is supplied from the puncture needle 100 to the artery-side blood line 12*a*, and then passes through the dialyzer 30 and is fed to the vein-side blood line 12*v*. The blood after purification flowing in the vein-side blood line 12*v* is returned back to the body of the patient via the puncture needle 100. In the dialyzer 30, unwanted components are removed from the blood of the patient and missing components are added.

Normally, prior to the dialysis treatment, the priming process, which is a process to expel air by causing the liquid (priming liquid) to flow in the blood circuit 10 and the dialyzer 30 is performed. The priming process will be described with reference to FIG. 3. In the present exemplary embodiment, the vein-side blood line 12*v* is connected to the supply line 54*s*, and the artery-side blood line 12*a* is connected to the discharge line 54*d* respectively for the priming process as illustrated in FIG. 3. When this connecting state is achieved, in the present exemplary embodiment, a first priming process for causing the priming liquid to flow in the axial direction of the dialyzer 30 and a second priming process for causing the priming liquid to flow in a circumferential direction of the dialyzer 30 are performed in sequence. In the first priming process, the blood pump PB is reversely driven with the introduction valve VI closed and the supply valve VS opened. Accordingly, the dialysate solution that functions as the priming liquid flows in the direction indicated by an arrow A in FIG. 3. In other words, the dialysate solution (priming liquid) supplied from the dialysate solution supplying and discharging apparatus 50 flows to the supply line 54*s*, the vein-side blood line 12*v*, the dialyzer 30, the artery-side blood line 12*a*, and the discharge line 54*d* in this order, and finally, is discharged in the dialysate solution supplying and discharging apparatus 50. At this time, the dialysate solution flows in the axial direction of the dialyzer 30 and passes mainly inside the hollow fiber membrane provided in the interior of the dialyzer 30.

In the second priming process, the introduction pump PI and the outlet pump PO are driven normally with the introduction valve VI opened and the supply valve VS closed. Accordingly, the dialysate solution that functions as the priming liquid flows in the direction indicated by an arrow B in FIG. 3. In other words, the dialysate solution supplied from the dialysate solution supplying and discharging apparatus 50 flows to the introduction line 52*i*, the dialyzer 30, and the outlet line 52*o* in this order, and is finally discharged in the dialysate solution supplying and discharging apparatus 50. At this time, the dialysate solution is supplied from the side of the dialyzer 30, and mainly passes through an outer periphery of the hollow fiber membrane in the dialyzer 30. In other words, by performing the first priming process and the second priming process, the dialysate solution (priming liquid) can be made to flow inside and outside the hollow fiber membrane, and thus air in the interior of the dialyzer 30 may be reliably expelled.

When performing such a priming process as described above, connection of the vein-side blood line 12*v* to the supply line 54*s* and connection of the artery-side blood line 12*a* to the discharge line 54*d* are necessary, as described above. For enabling such connections, the dialysis apparatus is provided with the supply port 56*s* secured to the supply line 54*s* and discharge port 56*d* secured to the discharge line 54*d*. Direct connection of the shunt connectors 18 to the supply and discharge ports 56 is also conceivable. In this case, however, likelihood of occurrence of the erroneous connection is high.

In other words, the two shunt connectors 18 have the same shape so as to be compatible with the versatile puncture needles 100, as described thus far. Therefore, when the supply and discharge ports 56 are configured to be connectable with the shunt connectors 18, the supply port 56*s* and the discharge port 56*d* also have the same shape. When the shape is the same in this manner, connection in combinations opposite from the original, that is, connection between the vein-side shunt connector 18*v* and the discharge port 56*d* and connection between the artery-side shunt connector 18*a* and the supply port 56*s* is also possible. When connection in combinations opposite from the original (erroneous connection) occurs, the priming liquid cannot be made to flow adequately.

In order to prevent the erroneous connection, forming the shunt connectors 18 into specific shapes which only allow connection to the corresponding supply and discharge ports 56 is conceivable. However, in this case, compatibility with the versatile puncture needles 100 is removed and the versatility of the blood circuit 10 is lowered. As another countermeasure, providing each of the shunt connectors 18 with a flange-shaped member therearound, which allows connection only to the corresponding supply and discharge ports 56, is also conceivable. In this configuration, erroneous connection is prevented while maintaining the versatility of the shunt connectors 18. However, when bulky members such as the flange-shaped members are provided in the vicinity of the shunt connectors 18, the flange-shaped members become obstacles when routing the blood lines 12, and hence the operability may be lowered.

Accordingly, in the present exemplary embodiment, the adapters 20 are provided respectively on the shunt connectors 18 in advance. The adapters 20 are members to be connected to the shunt connectors 18 and are capable of being connected to the corresponding supply and discharge ports 56 as described above, and thus are members that allow communication between the shunt connectors 18 and the corresponding supply and discharge ports 56 by being connected to the corresponding supply and discharge ports 56. The shapes of the port connecting portions Cpa and Cpv of the adapters 20 to be connected with the supply and discharge ports 56 are different from each other. Specifically, the port connecting portion Cpv of the vein-side adapter 20*v* has an outer diameter smaller than that of the port connecting portion Cpa of the artery-side adapter 20*a*. The shapes of the supply and discharge ports 56 are also different from each other so as to match the shapes of the adapters 20. Specifically, the diameter of an insertion port of the supply port 56*s* is smaller than the diameter of an insertion port of the discharge port 56*d*. Therefore, even when an attempt is made to insert the vein-side adapter 20*v* into the discharge port 56*d*, the vein-side adapter 20*v* cannot be fitted to the discharge port 56*d* (coupled in a liquid tight manner) because the outer diameter of the vein-side adapter 20*v* is smaller than the outer diameter of the discharge port 56*d*. When an attempt is made to insert the artery-side adapter 20*a* into the supply port 56*s*, insertion is not possible because the outer diameter of the artery-side adapter 20*a* is larger than that of the supply port 56*s*. In other words, the respective adapters 20 are configured to be capable of insertion into only the corresponding supply and discharge ports 56.

The blood circuit 10 is shipped in a state in which the adapters 20 are connected to the shunt connectors 18. The operator then sets the adapters 20 in the dialysis apparatus in a state of being attached to the shunt connectors 18 when using the blood circuit 10. Normally, the priming process is performed prior to the dialysis treatment. Therefore, the blood lines 12 of the blood circuits 10 are connected to the corresponding supplying and discharging lines 54 as illustrated in FIG. 3. At this time, the artery-side adapter 20a is attached to the artery-side shunt connector 18a and thus is capable of being connected only to the discharge port 56d. Likewise, the vein-side adapter 20v is attached to the vein-side shunt connector 18v and thus is capable of being connected only to the supply port 56s. Consequently, erroneous connection of the respective blood lines 12 is reliably prevented.

When the priming process is completed, the operator removes the adapters 20 from the supply and discharge ports 56 and releases the connection between the blood lines 12 and the supplying and discharging lines 54. Subsequently, the adapters 20 are removed from the shunt connectors 18 for the dialysis treatment, and the puncture needles 100 are attached instead. At this time, the shunt connectors 18 have a shape in conformance with the specific standard, and thus the versatile puncture needles 100 may be attached. Since the member or the like for preventing erroneous connection is not provided in the vicinity of each of the shunt connectors 18, high operability is maintained. In other words, according to the present exemplary embodiment, erroneous connection of the blood lines 12 is prevented reliably with the versatility and operability of the blood circuit 10 maintained.

FIG. 4 and FIG. 5 are drawings illustrating an example of the adapter set. FIG. 4 is a front view of the adapter set and FIG. 5 is a drawing of the adapter set viewed from the port connecting portions Cpa and Cpv side. As illustrated in FIG. 4 and FIG. 5, the artery-side adapter 20a and the vein-side adapter 20v are both a substantially rectangular parallelepiped block shaped member including a flow channel 40 formed at a center thereof for allowing the priming liquid to flow. One end of each of the flow channels 40 is provided with the connector connecting portion Cc which allows insertion of a distal end of the shunt connector 18. The connector connecting portions Cc on the vein side and the artery side have the same shape in conformance with the standard.

The port connecting portions Cpa and Cpv which are configured to be inserted into the supply and discharge ports 56 are provided at ends of the flow channels 40 on the other side, respectively. The port connecting portions Cpa and Cpv on the vein side and the artery side have the same inner diameter, and the outer diameter of the port connecting portion Cpv of the vein-side adapter 20v is smaller than the outer diameter of the port connecting portion Cpa of the artery-side adapter 20a. With the port connecting portions Cpa and Cpv having different outer diameters, connection is allowed only with the corresponding supply and discharge ports 56 and the erroneous connection of the blood lines 12 is prevented.

The artery-side adapter 20a and the vein-side adapter 20v of the present exemplary embodiment are configured to be coupled to each other. In other words, claw members 42 are formed to project from four corners on one side surface of the artery-side adapter 20a, and a substantially rectangular recess 44 is formed at a center of the one side surface. Likewise, a projection 46 having a shape corresponding to the recess 44 is formed at a center of one side surface of the vein-side adapter 20v. A front surface and a back surface of the vein-side adapter 20v are provided with shoulders 48 that allow the claw members 42 to engage the artery-side adapter 20a. The vein-side adapter 20v is pressed against the artery-side adapter 20a so that the projection 46 fits the recess 44, and the claw members 42 engage the shoulders 48, so that the artery-side adapter 20a and the vein-side adapter 20v are coupled and integrated. In this manner, when the two adapters 20a and 20v are integrated, two of the blood lines 12 are connected to two of the supplying and discharging lines 54 by only one step of inserting the integrated integral member into the supply and discharge ports 56.

Provided on lateral sides of the artery-side adapter 20a and the vein-side adapter 20v are holding portions 49 to be held by the operator when both members are integrated. The holding portions 49 are leaf spring shaped members extending from lateral sides of the respective adapters 20 on the other side in a cantilevered beam shape. The operator holds the holding portions 49 with fingers and inserts the integral member into the supply and discharge ports 56.

Note that the configurations of the blood circuit 10 and the adapter set described thus far are an example only, and configurations may be modified as appropriate as long as the adapters 20 are attached respectively to each of the two shunt connectors 18, and at least one of the two adapters 20 is configured to be connectable only to the corresponding one of the supply and discharge ports 56. For example, outline shapes of the port connecting portions Cpa and Cpv may be differentiated between the artery side and the vein side instead of the outer diameters. For example, a configuration in which the port connecting portion Cpa of the artery-side adapter 20a is formed into a substantially square shape in cross section, while the port connecting portion Cpv of the vein-side adapter 20v is formed into a triangular shape in cross section, is also applicable. Alternatively, the following configuration is also applicable. A wing member is provided on one of the adapter and the supply and discharge ports so as to project to the other one, a hole portion for receiving the wing member may be provided in the other one, and the shapes of the wing members and the hole portions are differentiated between the vein side (supply side) and the artery side (discharge side).

In the following description, the shapes of the adapters 20 are differentiated between the artery side and the vein side. However, elements other than the shape may be differentiated as long as only the connection is only allowed to the corresponding one of the supply and discharge ports 56. For example, magnets having opposite polarities may be embedded in the artery-side adapter 20a and the vein-side adapter 20v. For example, a magnet is disposed on an end surface of the port connecting portion Cpa of the artery-side adapter 20a so that an N-pole is exposed to the outside, and a magnet is disposed on an end surface of the port connecting portion Cpv of the vein-side adapter 20v so that an S-pole is exposed to the outside. Likewise, a magnet is disposed on an end surface of the supply port 56s so that an N-pole is exposed to the outside, and a magnet is disposed on an end surface of the discharge port 56d so that an S-pole is exposed to the outside. In this configuration, resistance is generated by magnetic repulsion when an attempt is made to connect the adapter 20 to the supply and discharge ports 56 which does not correspond thereto, and thus the operator easily becomes aware of erroneous connection. Consequently, erroneous connection of the blood lines 12 is reliably prevented. In the example illustrated in FIG. 4, the artery-side adapter 20a and the vein-side adapter 20v formed separately are fitted and integrated. However, the artery-side adapter 20*a* and the vein-side adapter 20*v* may be formed as an inseparable unitary part.

The exemplified blood circuit 10 is provided only with the air trap chamber 14 in the middle of the blood lines 12. However, the configuration of the blood circuit 10 may be modified as appropriate depending on the application and the like. For example, in addition to the air trap chamber 14, an access port for injecting medical agent such as anticoagulant may be additionally provided in the middle of the blood lines 12. The blood circuit 10 may further include a fluid infusion line that joins the middle of the blood lines 12 and allows a fluid infusion to be added to blood to flow therein. The blood circuit 10 may have a pressure monitor line or the like for detecting a pressure.

The blood circuit 10 of the present exemplary embodiment may be applied to treatment methods other than the hemodialysis as long as it is used for blood purification. For example, the blood circuit 10 may be applied to blood filtering using a filter (hemofilter) as the blood purifier, a simple plasma exchange using a plasma separator as the blood purifier, or a direct blood perfusion or the like using a blood purification column as a blood purifier. In these treatment methods, additional supply of fluid infusion to blood is required. Therefore, the fluid infusion line is connected to one of the artery-side blood line 12*a* and the vein-side blood line 12*v*. In these treatment methods, the blood purifier is not connected to the introduction line 52*i* because the supply of dialysate solution is not necessary. Therefore, in this case, a second priming process using the introduction line 52*i* and the outlet line 52*o* is not performed for priming.

Although only the example in which the supply and discharge ports 56 are provided on the dialysis apparatus has been described, the supply and discharge ports 56 may be provided outside the dialysis apparatus. For example, when the physiological saline solution is used as the priming liquid, the supply port 56*s* may be provided on a flexible bag filled with the physiological saline solution. When the priming liquid after use is discharged to a container or the like such as a tank or a bottle provided outside the dialysis apparatus, the discharge port 56*d* may be provided in such a container.

Figure 6:
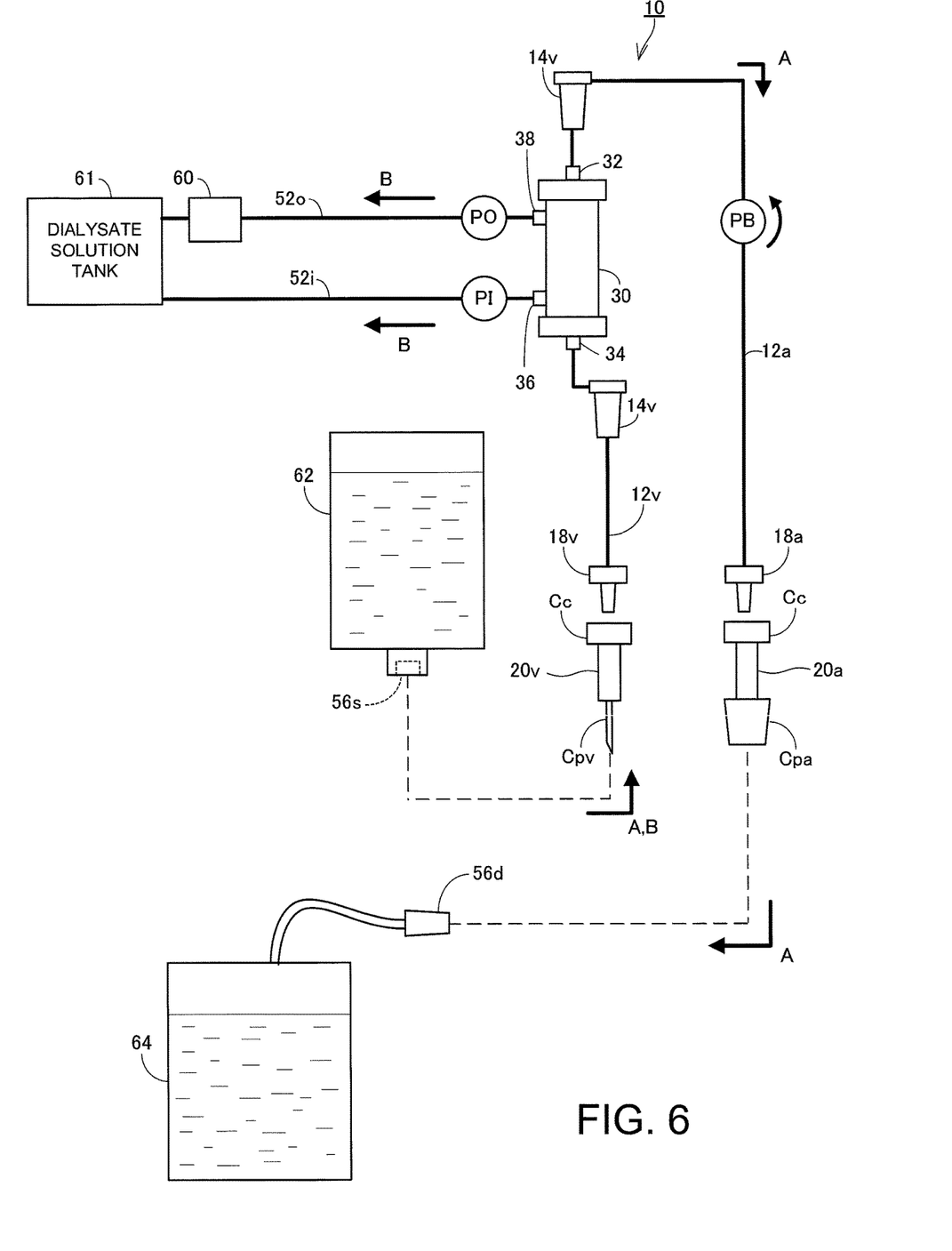
FIG. 6 is a drawing illustrating an example in which supply and discharge ports 56 are provided outside a dialysis apparatus.

FIG. 6 is a drawing illustrating an example in which supply and discharge ports 56 are provided outside a dialysis apparatus. The dialysis apparatus includes the blood pump PB, the introduction pump PI, the outlet pump PO, the introduction line 52*i*, and the outlet line 52*o* in the same manner as the dialysis apparatus illustrated in FIG. 2. In contrast, the dialysis apparatus does not include the dialysate solution supplying and discharging apparatus 50, the supply line 54*s*, and the discharge line 54*d*, but, unlike the dialysis apparatus illustrated in FIG. 2, includes a dialysate solution tank 61 and a dialysate solution reproduction column 60 instead. A dialysate solution is stored in the dialysate solution tank 61. The dialysate solution reproduction column 60 is provided between the outlet pump PO and the dialysate solution tank 61, and the dialysate solution after use, which is collected from the dialyzer 30, is purified to a reusable state. The dialysate solution reproduced from the dialysate solution reproduction column 60 is sent to the dialysate solution tank 61 and is used again for blood purification.

In such a dialysis apparatus, prior to the dialysis treatment, the priming process, which is a process to expel air by flowing the liquid (priming liquid) in the blood circuit 10 and the dialyzer 30, is performed. When performing the priming process, the blood circuit 10 is connected to a supply container 62 filled with the priming liquid and a discharge container 64 for storing the priming liquid after use.

The supply container 62 is not specifically limited as long as it is a container filled with the priming liquid. However, for example, a flexible bag filled with the physiological saline solution, that is, a physiological saline solution bag, may be used. The physiological saline solution bag is generally commercially available, and is provided with a cap having a rubber plug attached to a port. The rubber plug includes one or more puncture-type ports for receiving puncture of a needle, and the puncture-type port functions as the supply port 56*s* for supplying the priming liquid.

The discharge container 64 is not specifically limited as long as it can store the priming liquid after use, and for example, a tank, a flexible bag, a bottle, and the like may be used. However, in any container of the fours described above, the discharge container 64 includes the discharge port 56*d* in a form different from the supply port 56*s*. In the example illustrated in FIG. 6, the discharge port 56*d* of the discharge container 64 has a lure taper shape.

The blood circuit 10 is provided with an adapter set including the vein-side adapter 20*v* (second adapter) corresponding to the puncture-type supply port 56*s* and the artery-side adapter 20*a* (first adapter) corresponding to the puncture-type discharge port 56*d* of the lure taper shape. The artery-side adapter 20*a* is connected to the artery-side shunt connector 18*a*, and the vein-side adapter 20*v* is connected to the vein-side shunt connector 18*v*, both in a disconnectable manner. In FIG. 6, the shunt connectors 18 and the adapters 20 are illustrated separately for the sake of easy visual understanding. In fact, however, the blood circuit 10 is shipped in a state in which the corresponding adapters 20 are attached respectively to the shunt connectors 18 in the same manner as the blood circuit 10 illustrated in FIG. 1.

The two adapters 20*a* and 20*v* both have a substantially tubular shape having a flow channel penetrating therethrough in an axial direction. Each of the two adapters 20*a* and 20*v* is both provided at the first end thereof with the connector connecting portion Cc and at the second end thereof with the port connecting portion Cp. The connector connecting portions Cc have the same shape on the artery side and the vein side, and are connectable to the shunt connectors 18*v* and 18*a* having the shape in conformance with the specific standard.

In contrast, the port connecting portions Cp have shapes different from each other on the artery side and the vein side. Specifically, the port connecting portion Cpv on the vein side have the needle shape connectable to the puncture-type supply port 56*s*. In contrast, the port connecting portion Cpa on the artery side has a lure taper shape connectable to the lure taper shaped discharge port 56*d*. Therefore, the port connecting portion Cpv (the needle shape) on the vein side cannot be connected to the discharge port 56*d* having the lure taper shape, and the port connecting portion Cpa (lure taper shape) on the artery side cannot be connected to the puncture type supply port 56*s*. Consequently, erroneous connection of the port connecting portions Cp in the priming process can be effectively prevented.

Next, the priming process in this dialysis apparatus will be described. The vein-side blood line 12*v* is connected to the supply container 62, and the artery-side blood line 12*a* is connected to the discharge container 64 respectively for the priming process as illustrated in FIG. 6. Specifically, the vein-side adapter 20*v* attached to the distal end of the vein-side blood line 12*v* is connected to the supply port 56*s* provided on the supply container 62. Likewise, the artery-side adapter 20a provided at a distal end of the artery-side blood line 12a is connected to the discharge port 56d provided on the discharge container 64. At this time, as described above, the shape of the port connecting portions Cp is different between the artery side and the vein side, and thus erroneous connection of the port connecting portions Cp can be effectively prevented.

When adequate connection is successful, a first priming process for causing the priming liquid to flow in the axial direction of the dialyzer 30 and a second priming process for causing the priming liquid to flow in a circumferential direction of the dialyzer 30 are performed in sequence. In the first priming process, the blood pump PB is reversely driven with the introduction pump PI and the outlet pump PO stopped. Accordingly, the physiological saline solution that functions as the priming liquid flows in a direction indicated by an arrow A in FIG. 6. In other words, the physiological saline solution (priming liquid) supplied from the supply container 62 flows through the supply container 62, the vein-side blood line 12v, the dialyzer 30, the artery-side blood line 12a, and the discharge container 64 in this order. At this time, the dialysate solution flows in the axial direction of the dialyzer 30, and passes mainly inside the hollow fiber membrane provided in the interior of the dialyzer 30.

In the second priming process, the introduction pump PI is reversely driven and the outlet pump PO is normally driven with the blood pump PB stopped. Accordingly, the physiological saline solution that functions as the priming liquid flows in the direction indicated by an arrow B in FIG. 6. In other words, the physiological saline solution supplied from the supply container 62 flows through the vein-side blood line 12v, the dialyzer 30, the introduction line 52i and the outlet line 52o (dialysate solution reproduction column) and the dialysate solution tank 61 in this order and is finally stored in the dialysate solution tank 61. The physiological saline solution stored in the dialysate solution tank 61 may be discarded after the priming process. At this time, the dialysate solution is supplied from the side of the dialyzer 30, and mainly passes through an outer periphery of the hollow fiber membrane in the dialyzer 30. In other words, by performing the first priming process and the second priming process, the dialysate solution (priming liquid) can be made to flow inside and outside the hollow fiber membrane, and thus air in the interior of the dialyzer 30 may be reliably expelled.

In any case, the shunt connectors 18 and the supply and discharge ports 56 are brought into communication with the blood circuit 10, and the adapter sets having different configurations are provided on the vein side and the artery side, so that erroneous connection at the time of the priming process is effectively prevented without impairing the versatility and the operability of the blood circuit 10.

Figure 7:
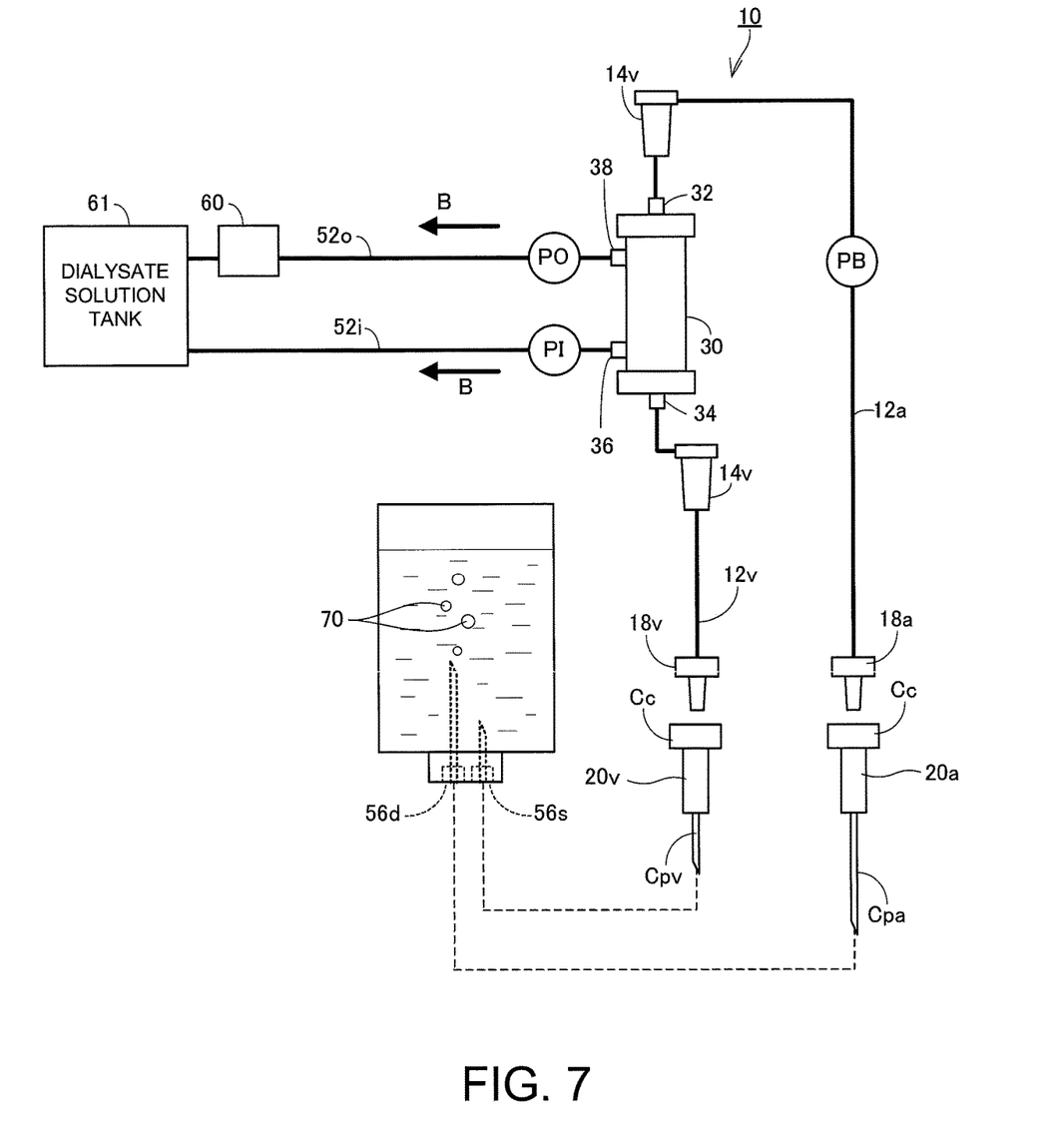
FIG. 7 is a drawing illustrating a configuration of a reference example.

Referring now to FIG. 7, a reference example will be described as a complementary description. The blood circuit 10 illustrated in FIG. 7 is similar to the blood circuit 10 illustrated in FIG. 6. However, the blood circuit 10 illustrated in FIG. 7 uses a single supplying and discharging container 66 including a supply container and a discharge container integrated with each other for the priming process. The supplying and discharging container 66 is not specifically limited as long as the container is filled with the priming liquid. However, in the example illustrated in FIG. 7, a physiological saline solution bag with a rubber plug attached thereto is used as the supplying and discharging container 66. The supplying and discharging container 66 is provided with the rubber plug having a plurality of puncture-type ports. One of the ports functions as the supply port 56s, and another one functions as the discharge port 56d. However, the plurality of puncture-type ports provided in the rubber plug all have the same configuration, and thus any of the puncture-type ports may be used as the supply port 56s or the discharge port 56d.

The blood circuit 10 is provided with an adapter set including the artery-side adapter 20a (first adapter) corresponding to the puncture-type supply port 56s and the vein-side adapter 20v (second adapter) corresponding to the puncture-type discharge port 56d of the same puncture type. Each of these adapters 20a and 20v includes the connector connecting portion Cc and the port connecting portion Cp. The connector connecting portions Cc on the artery side and the vein side have the same shape. In contrast, the port connecting portions Cp on the artery side and the vein side have a needle shape having the same diameter. However, the artery-side port connecting portion Cpa is longer than the vein-side port connecting portion Cpv.

When the priming process is performed prior to the dialysis treatment, the artery-side port connecting portion Cpa and the vein-side port connecting portion Cpv are connected to the puncture type port provided in the rubber plug. Again, the plurality of puncture type ports have the same shape, and thus the artery-side port connecting portion Cpa and the vein-side port connecting portion Cpv may be connected to any puncture type port. As a result, the port where the artery-side port connecting portion Cpa is punctured functions as the discharge port 56d, and the port where the vein-side port connecting portion Cpv is punctured functions as the supply port 56s.

In FIG. 7, the port connecting portions Cp punctured in the supply and discharge ports 56s and 56d are indicated by broken lines. As illustrated in FIG. 7, when the port connecting portions Cp are pushed inward up to root portions into the supply and discharge ports 56s and 56d, the height of the distal ends of the port connecting portions Cpa and Cpv become different due to the difference in length of the port connecting portions Cpa and Cpv on the artery side and the vein side. Specifically, when punctured from the lower side of the rubber plug provided at the lower end of the supplying and discharging container 66, the distal end of the artery-side port connecting portion Cpa comes to a position higher than the distal end of the vein-side port connecting portion Cpv. In other words, by changing the shape (length) of the port connecting portion Cpv between the artery side and the vein side, a suction port (distal end of the vein-side port connecting portion Cpv) of the priming liquid and a discharge port (distal end of the artery-side port connecting portion Cpa) may be reliably changed.

The reason why the positions of the suction port and the discharge port of the priming liquid are changed will be described. When the priming process is performed, a first priming process for causing the priming liquid to flow in the axial direction of the dialyzer 30 and a second priming process for causing the priming liquid to flow in a circumferential direction of the dialyzer 30 are performed in sequence. In the first priming process, the blood pump PB is reversely driven with the introduction pump PI and the outlet pump PO stopped. Accordingly, the physiological saline solution that functions as the priming liquid flows in a direction indicated by an arrow A in FIG. 6. In other words, the physiological saline solution (priming liquid) supplied from the supplying and discharging container 66 flows through the supplying and discharging container 66, the vein-side blood line 12v, the dialyzer 30, the artery-side blood line 12a, and the supplying and discharging container 66 in this order. At this time, the dialysate solution flows in the axial direction of the dialyzer 30 and passes mainly inside the hollow fiber membrane provided in the interior of the dialyzer 30. The procedure of the second priming process is the same as the exemplary embodiment described above, and thus description will be omitted. By using the supplying and discharging container 66 including the supply part and the discharge part of the priming liquid integrated with each other, the number of containers to be used for priming may be reduced, and thus the configuration may be further simplified.

Here, the priming liquid discharged from the distal end of the artery-side port connecting portion Cpa contains air (air bubbles 70) collected in the course of passing through the blood circuit 10 and the dialyzer 30. When such air flows into the blood circuit 10 again via the vein-side port connecting portion Cpv, air cannot be expelled sufficiently from the blood circuit, and thus an insufficient priming process, or elongation of time taken to complete the priming process, may result.

In the blood circuit 10 illustrated in FIG. 7, as described above, the artery-side port connecting portion Cpa is longer than the vein-side port connecting portion Cpv, and the discharge port of the priming liquid is higher than the suction port. In this case, the air bubbles 70 discharged from the artery-side port connecting portion Cpa do not pass near the vein-side port connecting portion Cpv in the course of floating upward. Consequently, suction of the air bubbles 70 by the vein-side port connecting portion Cpv is effectively prevented, and thus the priming process may be performed more appropriately.

REFERENCE SIGNS LIST 10 blood circuit
12a artery-side blood line
12v vein-side blood line
14 air trap chamber
16a artery-side dialyzer connector
16v vein-side dialyzer connector
18a artery-side shunt connector
18v vein-side shunt connector
20a artery-side adapter
20v vein-side adapter
30 dialyzer
32 blood entry port
34 blood exit port
36 introduction port
38 outlet port
40 flow channel
42 claw member
44 recess
46 projection
48 shoulder
49 holding portion
50 dialysate solution supplying and discharging apparatus
52i introduction line
52o outlet line
54d discharge line
54s supply line
56d discharge port
56s supply port
60 dialysate solution reproduction column
61 dialysate solution tank
62 supply container
64 discharge container
66 supplying and discharging container
70 air bubbles
100 puncture needle
Cc connector connecting portion
Cpa, Cpv port connecting portion
PB blood pump
PI introduction pump
PO outlet pump
VI introduction valve
VS supply valve

The invention claimed is:

1. A blood circuit comprising:
a blood line that is placed outside of a body and is configured to have blood flow therethrough;
a first connector that includes a first end and a second end, and is attached at the first end thereof to the blood line and is configured to be connected at the second end thereof to a puncture needle; and
a second connector that includes a first end and a second end, and is attached at the first end thereof to the blood line and is configured to be connected at the second end thereof to a puncture needle, the first connector and the second connector allowing connection of puncture needles of a type identical to each other;
a first adapter that includes a first end and a second end, and is configured to be connected at the first end thereof to the first connector and connected at the second end thereof to a first port provided outside the blood circuit to allow communication between the first connector and the first port in a liquid-tight manner; and
a second adapter that includes a first end and a second end, and is configured to be connected at the first end thereof to the second connector and connected at the second end thereof to a second port provided outside the blood circuit to allow communication between the second connector and the second port in a liquid-tight manner, wherein:
the second end of the first adapter and the second end of the second adapter have different structures to prevent at least one of connection between the second end of the first adapter and the second port and connection between the second end of the second adapter and the first port, and
the blood circuit is a single blood circuit that comprises the first connector and the second connector, and the first adapter and the second adapter are configured to be connected to the single blood circuit at a same time.

2. The blood circuit according to claim 1, wherein a structure of the first end of the first adapter is identical to a structure of the first end of the second adapter.

3. The blood circuit according to claim 1, wherein the first adapter is configured to be connected to the second end of the first connector, and the second adapter is configured to be connected to the second end of the second connector.

* * * * *